United States Patent [19]
Gibbons

[11] 3,938,529
[45] Feb. 17, 1976

[54] INDWELLING URETERAL CATHETER

[76] Inventor: Robert P. Gibbons, 7310 Mercer Terrace Drive, Mercer Island, Wash. 98040

[22] Filed: July 22, 1974

[21] Appl. No.: 490,573

[52] U.S. Cl. ............................ 128/349 R; 128/350 R
[51] Int. Cl.² ........................................ A61M 25/00
[58] Field of Search ............ 128/348, 349 R, 349 B, 128/350 R

[56] References Cited
UNITED STATES PATENTS

| | | | |
|---|---|---|---|
| 2,211,975 | 8/1940 | Hendrickson | 128/349 R |
| 2,212,334 | 8/1940 | Wallerich | 128/349 R |
| 3,123,077 | 3/1964 | Alcamo | 128/335.5 |
| 3,308,819 | 3/1967 | Arp | 128/215 |
| 3,592,197 | 7/1971 | Cohen | 128/349 R |
| 3,783,454 | 1/1974 | Sausse | 128/348 X |
| 3,788,327 | 1/1974 | Donowitz et al. | 128/350 R |

*Primary Examiner*—Dalton L. Truluck
*Attorney, Agent, or Firm*—Seed, Berry, Vernon & Baynham

[57] ABSTRACT

A medical-grade, flexible tube is provided with a plurality of circumferentially and longitudinally spaced, flexible, directional anchoring protrusions for allowing the catheter to be moved lengthwise along a passage in one direction but to resist movement lengthwise out of the passage. Lateral apertures are provided at both ends of the tube for providing a fluid path into and out of the ends of the tube. An additional protrusion is provided at one end of the tube to resist lengthwise inward movement of the tube.

6 Claims, 2 Drawing Figures

INDWELLING URETERAL CATHETER

BACKGROUND OF THE INVENTION

1. Field of the Invention

This invention pertains to catheters and, more particularly, to indwelling ureteral catheters.

2. Description of the Prior Art

Indwelling ureteral stents or catheters have been used for ureteral drainage heretofore. The catheters were never widely accepted in the medical profession, however, since they frequently migrated out of the ureter, due primarily to peristaltic activity.

SUMMARY OF THE INVENTION

It is an object of this invention to provide an indwelling ureteral catheter that resists lengthwise outward movement in a ureter.

It is another object of this invention to provide an indwelling ureteral catheter that resists lengthwise movement of the tube both inwardly and outwardly of the ureter.

It is an object of this invention to provide an indwelling ureteral catheter that can be maintained in place for long periods of time.

Basically, these objects are obtained by providing a flexible tube of sufficient strength to minimize collapse of the walls of the tube, a plurality of apertures adjacent opposite ends of the tube, and a plurality of circumferentially and longitudinally spaced, flexible, directional anchoring means provided on the tube for allowing movement of the tube in one direction but resisting movement of the tube in the opposite direction.

In the preferred embodiment, the anchoring means are laterally extending barbs of flexible silicone rubber pointed outwardly and lengthwise in a rearward direction so that, as the catheter is inserted into the ureter, the barbs fold easily down against the outer wall of the tube and provide little resistance to movement. Once in place, however, the barbs will flex outwardly into engagement with the wall of the ureter, providing a wedging, anchoring connection with the ureter.

In the preferred embodiment, an additional flexible wing is placed on the rearward end of the tube to lightly anchor the tube additionally against the less forceful inward migration caused by the ureter activity on the tube.

DETAILED DESCRIPTION OF THE PREFERRED EMBODIMENT

Figure 1:
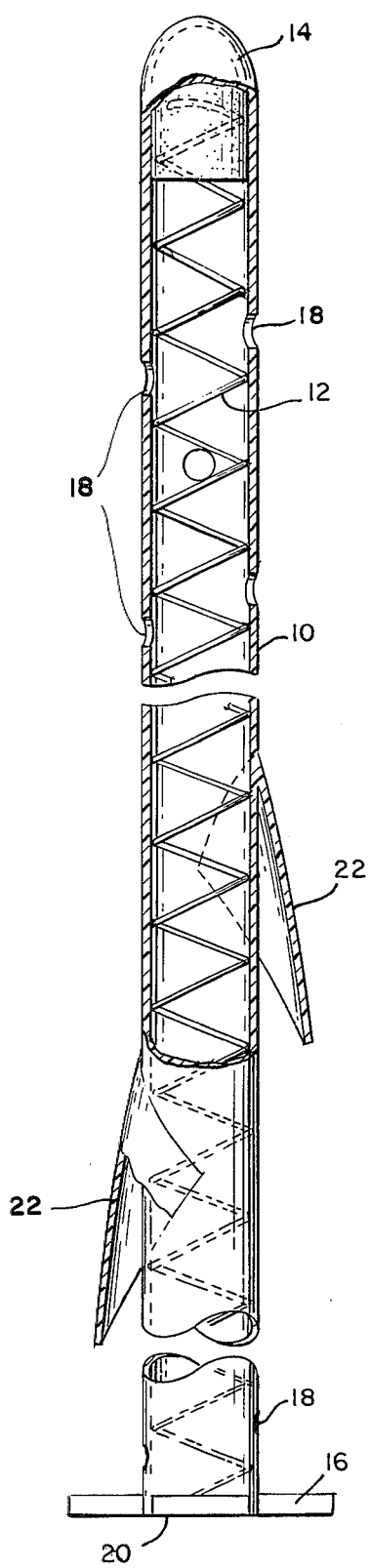
FIG. 1 is an enlarged side elevation, partially broken away for clarity, of a catheter embodying the principles of the invention.
Figure 2:
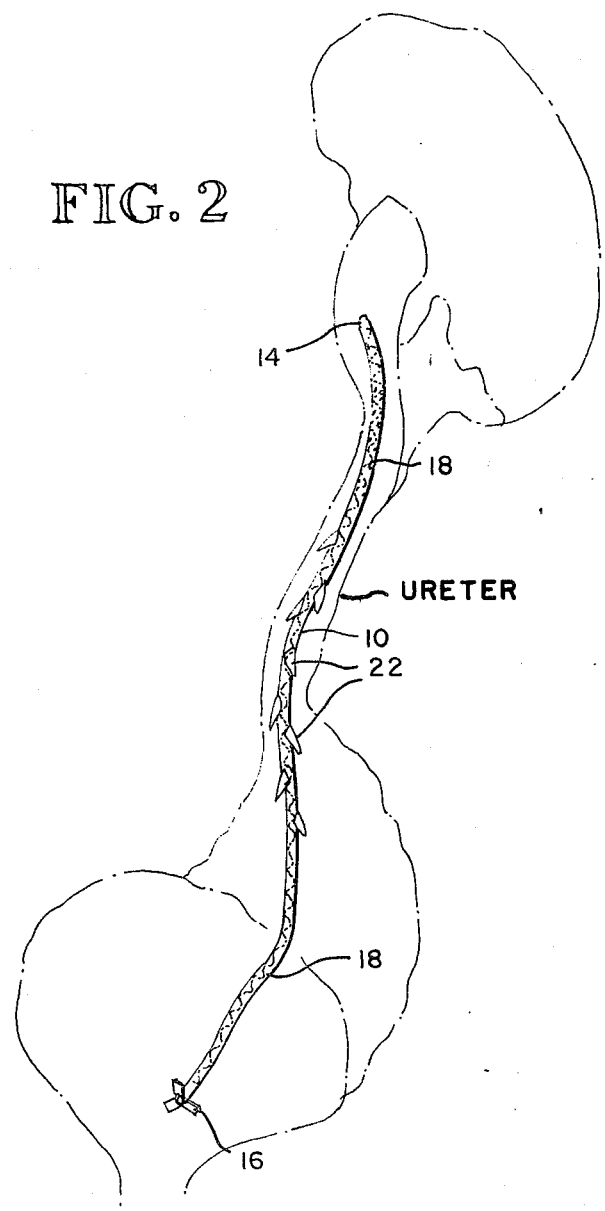
FIG. 2 is a schematic isometric illustrating the catheter in place in a ureter.

As best shown in FIG. 1, the catheter includes an elongated flexible tube 10, preferably of at least two sizes and lengths, approximately 15 and 23 centimeters long and between 6.5 F and 9 F outside diameter. The tube is of sufficient wall strength to prevent collapsing, such as by using an adequately thick wall or by adding a wire support coil 12. The forward end of the tube is beveled and sealed to form a conical, closed tip 14. The tip may be of radiopaque material for X-ray detection and serves to guide the tube during insertion into a ureter. The opposite end of the tube is provided with substantially circumferential but spaced wings 16 of flexible but relatively stiff silastic material to prevent inward migration of the tube through the ureter but have the flexibility and ability to collapse when inserted through a cystoscope or other insertion instrument.

Adjacent either end of the tube are a plurality of openings 18 which provide drain passages into and out of the tube. The tube also has an end opening 20.

A plurality of circumferentially spaced, flexible, laterally extending barbs 22 are provided lengthwise along the central portion of the tube intermediate the opposite ends. These barbs point rearwardly and outwardly but are sufficiently flexible that forward movement of the catheter in the ureter causes the barbs to flatten against the tube, providing little resistance to movement. Once in place, however, the barbs will flex outwardly into engagement with the wall of the ureter to wedge against the wall and restrict rearward or outward movement of the tube along the ureter.

All of the parts of the catheter are made of medical-grade silicone rubber.

Use of the catheter is readily apparent. The preferred procedure for inserting the catheter is with the use of a wire stylet inserted through a uretal catheter guide.

As is readily apparent, the tube provides a soft but non-collapsing catheter designed to maintain urine flow for extended periods of time in renal or ureteral fistulas, and when the ureter is obstructed, including treatable metastatic cancer, benign disease, and where etiology of obstruction has not yet been established. Several other advantages in use of the catheter are: no incision, no appliance or external catheter, reduced hospital time and costs, no interference with subsequent management, reduced morbidity, relative simplicity and reversibility.

The dentate protrusions and wing or collar at the distal end of the tube discourage both expulsion and upward migration, minimizing the necessity for replacement of the catheter. They are not so rigid that removal is not possible, however.

While the preferred embodiment of the invention has been illustrated and described, it should be understood that variations will be apparent to one skilled in the art without departing from the principles herein. Accordingly, the invention is not to be limited to the specific embodiment illustrated.

The embodiments of the invention in which a particular property or privilege is claimed are defined as follows:

1. An indwelling ureteral catheter comprising a medical-grade, flexible tube of sufficient strength to minimize collapse of the walls of the tube, a plurality of apertures adjacent opposite ends of the tube, and a plurality of circumferentially and longitudinally spaced, flexible, directional anchoring means provided generally adjacent the longitudinal center of the tube for allowing movement of the tube in one direction but resisting movement of the tube in the opposite direction, said anchoring means including soft, flexible, resilient, laterally and axial outwardly directed tips of a length sufficient to span the distance between the tube and the sidewall of the ureter and flexed radially outwardly with sufficient force to wedge against the sidewall of the ureter and hold the tube against axial outward movement caused by gravity or peristaltic activity, said tips having sufficient flexibility and softness to flatten outwardly against the tube during intentional outward movement of the tube during withdrawal so as not to penetrate the sidewall of the ureter, whereby the tube can be inserted into the ureter in one direction, remain lodged against outward movement caused by peristaltic activity, but be safely removed when required.

2. The catheter of claim 1, said tube including a closed, smooth, conical, firm inner end for guiding the tube during insertion.

3. The catheter of claim 2, anchoring means further including laterally extending, flexible and collapsible wing means at the outer end of the tube for providing resistance to movement of the tube in the outward direction for reducing inward migration of the tube.

4. The catheter of claim 1, including laterally extending, flexible and collapsible wing means at the outer end of the tube for resisting inward lengthwise movement of the tube in the ureter.

5. An indwelling ureteral catheter for an obstructed ureter comprising a medical-grade, flexible tube of sufficient strength to minimize collapse of the walls of the tube, a plurality of apertures adjacent opposite ends of the tube, and a plurality of axially and radially outwardly tapered, relatively large anchoring tips secured to the outside of the tube, said tips being located in approximately the axial central third of the tube and being spaced circumferentially and axially so as to provide an anchor regardless of the circumferential and longitudinal location of the obstruction along the ureter, said tips having sufficient resiliency and length to wedge radially outwardly against the sidewall of the ureter, but sufficient softness to collapse when the tube is moved axially inwardly of the ureter and collapse and not penetrate the sidewall of the ureter when the tube is moved intentionally axially outwardly of the ureter for removal of the catheter.

6. The catheter of claim 5, including laterally extended, flexible, circumferentially spaced wings attached to the axial outer end of the tube for resisting axial inward movement of the tube but being sufficiently flexible to collapse when intentionally radially compressed.

* * * * *